US011259890B2

(12) United States Patent
Evans

(10) Patent No.: US 11,259,890 B2
(45) Date of Patent: Mar. 1, 2022

(54) SURGICAL STAPLING INSTRUMENTS AND SURGICAL LOADING UNITS THEREOF

(71) Applicant: Covidien LP, Mansfield, MA (US)

(72) Inventor: Christopher Kelly Evans, Southington, CT (US)

(73) Assignee: Covidien LP, Mansfield, MA (US)

( * ) Notice: Subject to any disclaimer, the term of this patent is extended or adjusted under 35 U.S.C. 154(b) by 317 days.

(21) Appl. No.: 16/503,691

(22) Filed: Jul. 5, 2019

(65) Prior Publication Data

US 2021/0000563 A1    Jan. 7, 2021

(51) Int. Cl.
| | |
|---|---|
| *A61B 17/072* | (2006.01) |
| *A61B 90/00* | (2016.01) |
| *A61B 90/94* | (2016.01) |
| *A61B 17/068* | (2006.01) |
| *A61B 17/115* | (2006.01) |
| *A61B 17/00* | (2006.01) |

(52) U.S. Cl.
CPC ............ *A61B 90/08* (2016.02); *A61B 17/068* (2013.01); *A61B 17/072* (2013.01); *A61B 17/07207* (2013.01); *A61B 90/94* (2016.02); *A61B 17/115* (2013.01); *A61B 2017/00017* (2013.01); *A61B 2017/00473* (2013.01); *A61B 2017/07214* (2013.01); *A61B 2017/07257* (2013.01); *A61B 2017/07271* (2013.01); *A61B 2090/0805* (2016.02); *A61B 2090/0806* (2016.02)

(58) Field of Classification Search
CPC ................ A61B 17/068; A61B 17/072; A61B 17/07207; A61B 17/115; A61B 2017/00022; A61B 2017/00473; A61B 2017/00398; A61B 2017/00464; A61B 2017/00482; A61B 2017/00477; A61B 2017/07214; A61B 90/98
USPC .............. 227/19, 175.1, 175.2, 176.1, 180.1; 606/1, 139, 219
See application file for complete search history.

(56) References Cited

U.S. PATENT DOCUMENTS

| | | | |
|---|---|---|---|
| 6,793,652 | B1 | 9/2004 | Whitman et al. |
| 6,981,941 | B2 | 1/2006 | Whitman et al. |
| 8,763,879 | B2 | 7/2014 | Shelton, IV et al. |
| 8,960,520 | B2 | 2/2015 | McCuen |
| 9,000,720 | B2 | 4/2015 | Stulen et al. |
| 9,055,943 | B2 | 6/2015 | Zemlok et al. |
| 9,113,880 | B2 | 8/2015 | Zemlok et al. |

(Continued)

FOREIGN PATENT DOCUMENTS

| | | |
|---|---|---|
| EP | 2954854 A2 | 12/2015 |
| EP | 3409215 A1 | 12/2018 |

OTHER PUBLICATIONS

European Search Report dated Nov. 16, 2020, issued in corresponding EP Appln. No. 20183902, 11 pages.

*Primary Examiner* — Scott A Smith

(57) ABSTRACT

A surgical stapling instrument includes a handle assembly, a surgical loading unit, and an adapter assembly interconnecting the handle assembly and the surgical loading unit. The surgical loading unit includes a memory having stored therein instructions, which when executed by a processor of the handle assembly, override instructions stored in a memory of the handle assembly and implement an operating parameter of the surgical loading unit that is unique to a tissue type or a specific surgical procedure to be performed by the surgical loading unit.

8 Claims, 4 Drawing Sheets

(56) References Cited

U.S. PATENT DOCUMENTS

| | | |
|---|---|---|
| 9,636,112 B2 | 5/2017 | Penna et al. |
| 9,706,674 B2 | 7/2017 | Collins et al. |
| 2011/0121049 A1 | 5/2011 | Malinouskas et al. |
| 2015/0108201 A1 | 4/2015 | Williams |
| 2015/0122870 A1 | 5/2015 | Zemlok et al. |
| 2015/0209035 A1 | 7/2015 | Zemlok |
| 2015/0216525 A1 | 8/2015 | Collins et al. |
| 2015/0351765 A1* | 12/2015 | Valentine ............ G06F 11/1448 227/176.1 |
| 2016/0249921 A1 | 9/2016 | Cappola |
| 2016/0249929 A1 | 9/2016 | Cappola et al. |
| 2016/0265938 A1 | 9/2016 | Hryb |
| 2016/0310134 A1 | 10/2016 | Contini et al. |
| 2016/0345973 A1 | 12/2016 | Marczyk et al. |
| 2017/0333033 A1 | 11/2017 | Valentine et al. |

\* cited by examiner

SURGICAL STAPLING INSTRUMENTS AND SURGICAL LOADING UNITS THEREOF

BACKGROUND

Technical Field

The disclosure relates to surgical stapling instruments. More particularly, the disclosure relates to intelligent loading units of surgical stapling instruments.

Background of Related Art

Surgical stapling instruments for operating on tissue are well known in the art and may include a handle assembly, a body portion extending distally from the handle assembly, and a surgical loading unit supported on a distal end portion of the body portion. The surgical loading unit includes first and second jaws which are movable in relation to each other between unapproximated and approximated positions. In surgical stapling instruments, the first jaw is an anvil assembly and the second jaw is a cartridge assembly.

Surgical stapling instruments may be pre-programmed to adjust firing speed, clamping force, etc., based on properties of tissue being treated (e.g., tissue thickness). For example, when the tissue is determined to be relatively thick, instructions stored in the handle assembly of the surgical stapling instrument may cause the handle assembly to fire staples from the attached surgical loading unit and/or advance a knife bar at a reduced speed.

SUMMARY

In accordance with an aspect of the disclosure, a surgical loading unit for use with a surgical stapling instrument is provided. The surgical loading unit includes a staple cartridge assembly, an anvil assembly operably coupled to the staple cartridge assembly, and a memory associated with at least one of the staple cartridge assembly or the anvil assembly. The memory has instructions stored therein, which when executed, implement an operating parameter of the surgical loading unit. The operating parameter is unique to a tissue type or a specific surgical procedure to be performed by the surgical loading unit.

In aspects, the operating parameter may include a staple firing speed, a staple firing force, a clamping speed, and/or a clamping force of the surgical loading unit.

In aspects, the firing speed may be unique to the tissue type or the specific surgical procedure to be performed by the surgical loading unit.

In aspects, the firing force may be unique to the tissue type or the specific surgical procedure to be performed by the surgical loading unit.

In aspects, the specific surgical procedure to be performed by the surgical loading unit may include endoscopic gastro-intestinal anastomosis, tissue resection, or lesion resection.

In aspects, the memory may have data related to the surgical loading unit stored therein.

In aspects, the data may include a serial number of the surgical loading unit, a type of the surgical loading unit, a size of the surgical loading unit, a staple size included in the surgical loading unit, information identifying whether the surgical loading unit has been fired, a length of a firing stroke of the surgical loading unit, and/or a maximum number of uses of the surgical loading unit.

In aspects, the instructions stored in the memory, when executed, may override programming in a corresponding adapter assembly or handle assembly. The operating parameter may be different from an operating parameter in the programming.

In accordance with another aspect of the disclosure, a surgical stapling instrument is provided and includes a handle assembly and a surgical loading unit configured to be coupled to the handle assembly. The handle assembly includes a memory having instructions stored therein and a processor configured to execute the instructions. The surgical loading unit includes a staple cartridge assembly, an anvil assembly operably coupled to the staple cartridge assembly, and a memory. The memory has instructions stored therein, which when executed by the processor of the handle assembly, override the instructions stored in the memory of the handle assembly and implement an operating parameter of the surgical loading unit that is unique to a tissue type or a specific surgical procedure to be performed by the surgical loading unit.

In aspects, the operating parameter may include a staple firing speed, a staple firing force, a clamping speed, and/or a clamping force of the surgical loading unit.

In aspects, the firing speed may be unique to the tissue type or the specific surgical procedure to be performed by the surgical loading unit.

In aspects, the firing force may be unique to the tissue type or the specific surgical procedure to be performed by the surgical loading unit.

In aspects, the specific surgical procedure to be performed by the surgical loading unit may include endoscopic gastro-intestinal anastomosis, tissue resection, or lesion resection.

In aspects, the memory of the surgical loading unit may have data related to the surgical loading unit stored therein.

In aspects, the data may include at least one of a serial number of the surgical loading unit, a type of the surgical loading unit, a size of the surgical loading unit, a staple size, information identifying whether the surgical loading unit has been fired, a length of a firing stroke of the surgical loading unit, and/or a maximum number of uses of the surgical loading unit.

In aspects, the surgical stapling instrument may further include an adapter assembly configured to interconnect the surgical loading unit and the handle assembly.

In aspects, the instructions stored on the memory of the surgical loading unit may alter an operation of the adapter assembly.

In accordance with yet another aspect of the disclosure, a method of modifying an operation of a surgical stapling instrument is provided. The method includes transferring instructions from a memory of a surgical loading unit to a processor of an adapter assembly or a powered handle assembly of the surgical stapling instrument; and overriding instructions stored in a memory of the handle assembly or the adapter assembly with the instructions of the memory of the surgical loading unit. The instructions of the memory of the surgical loading unit direct the processor to adapt an operation of the adapter assembly or the handle assembly from a preset operation mode to a unique operation mode.

In aspects, the unique operation mode may adjust how the handle assembly or the adapter assembly effects functions of the surgical loading unit.

In aspects, the unique operation mode may correspond to a unique tissue type or a specific surgical procedure to be performed by the surgical loading unit.

Further details and aspects of exemplary embodiments of the disclosure are described in more detail below with reference to the appended figures.

BRIEF DESCRIPTION OF THE DRAWINGS

Embodiments of the disclosure are described herein with reference to the accompanying drawings, wherein.

DETAILED DESCRIPTION

Figure 1:
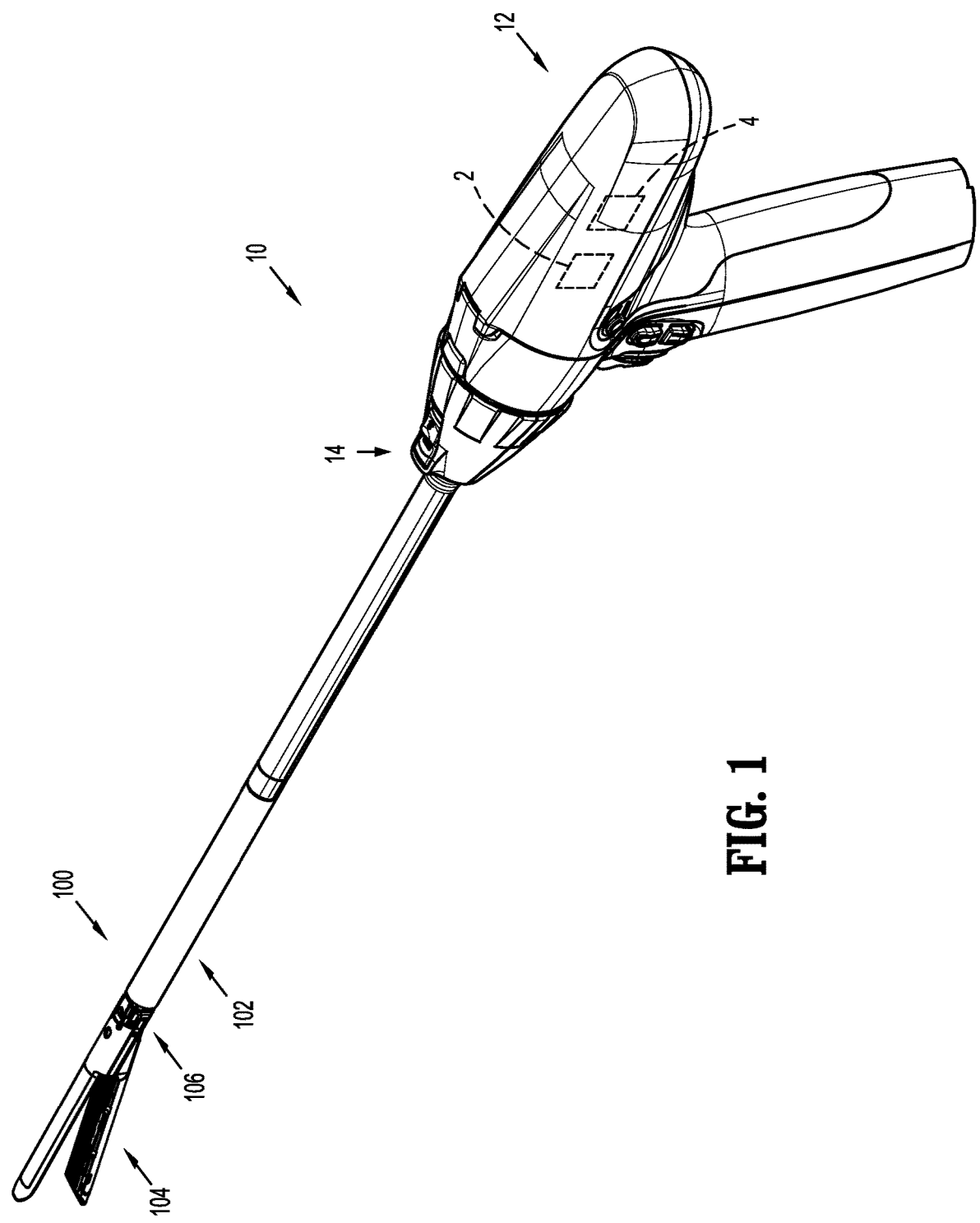
FIG. 1 is a perspective view of an embodiment of a surgical stapling instrument in accordance with the disclosure.

Embodiments of the disclosed surgical stapling instrument and surgical loading units thereof are described in detail with reference to the drawings, in which like reference numerals designate identical or corresponding elements in each of the several views. As used herein, the term "distal" refers to that portion of the surgical stapling instrument or component thereof that is closest to the patient, while the term "proximal" refers to that portion of the surgical stapling instrument or component thereof further from the patient.

As will be described in detail below, provided is a surgical loading unit for use in a surgical stapling instrument. The surgical loading unit includes an anvil assembly, a staple cartridge assembly pivotably coupled to the anvil assembly, and a memory. The memory has instructions stored therein that are unique to a type of tissue the surgical loading unit is intended to be used on, or a type of surgical procedure that the surgical loading unit is intended to be used in. The memory is configured to transfer the instructions from the surgical loading unit to a processor in a handle assembly of the surgical stapling instrument. The instructions direct the processor to override programming stored in the handle assembly, such that the processor carries out a function(s) of the surgical loading unit in the manner prescribed by the instructions stored in the memory of the surgical loading unit. Other features and benefits of the disclosed surgical stapling instruments are further detailed below.

FIG. 1 illustrates an embodiment of the disclosed surgical stapling instrument 10. The surgical stapling instrument 10 includes a powered handle assembly 12, an adapter assembly 14, and a surgical loading unit 100. The handle assembly 12 and the adapter assembly 14 are configured to effect operation of the loading unit 100. The handle assembly 12 is configured for selective connection with the adapter assembly 14, and, in turn, the adapter assembly 14 is configured for selective connection with single use loading units ("SULU's") 100. The handle assembly 12 includes a processor 2 for effecting operation of drive motors (not shown) in the handle assembly 12, and a memory 4 having stored therein instructions or programs to be executed by the processor 2.

Although the loading unit 100 is shown and described as being selectively secured to the adapter assembly 14 of the surgical stapling instrument 10, it is envisioned that the loading unit 100 may be supported on a shaft of the handle assembly 12 in embodiments where the surgical stapling instrument 10 is devoid of an adapter assembly.

For a detailed description of the structure and function of the handle assembly 12 and the adapter assembly 14, please refer to commonly owned U.S. Pat. No. 9,055,943 and U.S. Patent Application Publication No. 2016/0310134, the entire contents of each of which are incorporated by reference herein. Details regarding the operation of the loading unit 100 may be found in U.S. Patent Application Publication No. 2016/0249929, the entire contents of which are hereby incorporated by reference herein.

Figure 2:
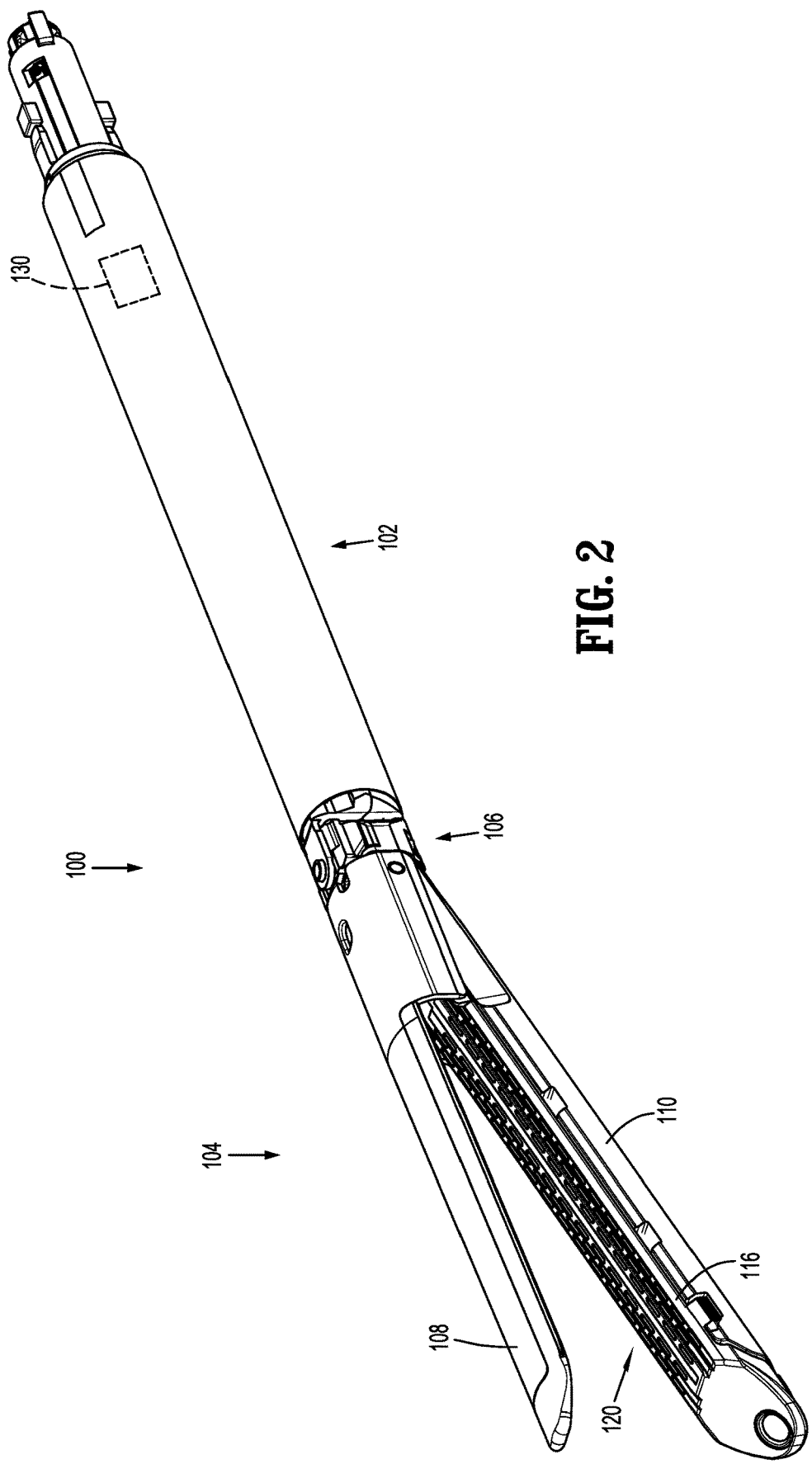
FIG. 2 is a side, perspective view of a surgical of the surgical stapling instrument shown in FIG. 1.
Figure 3:
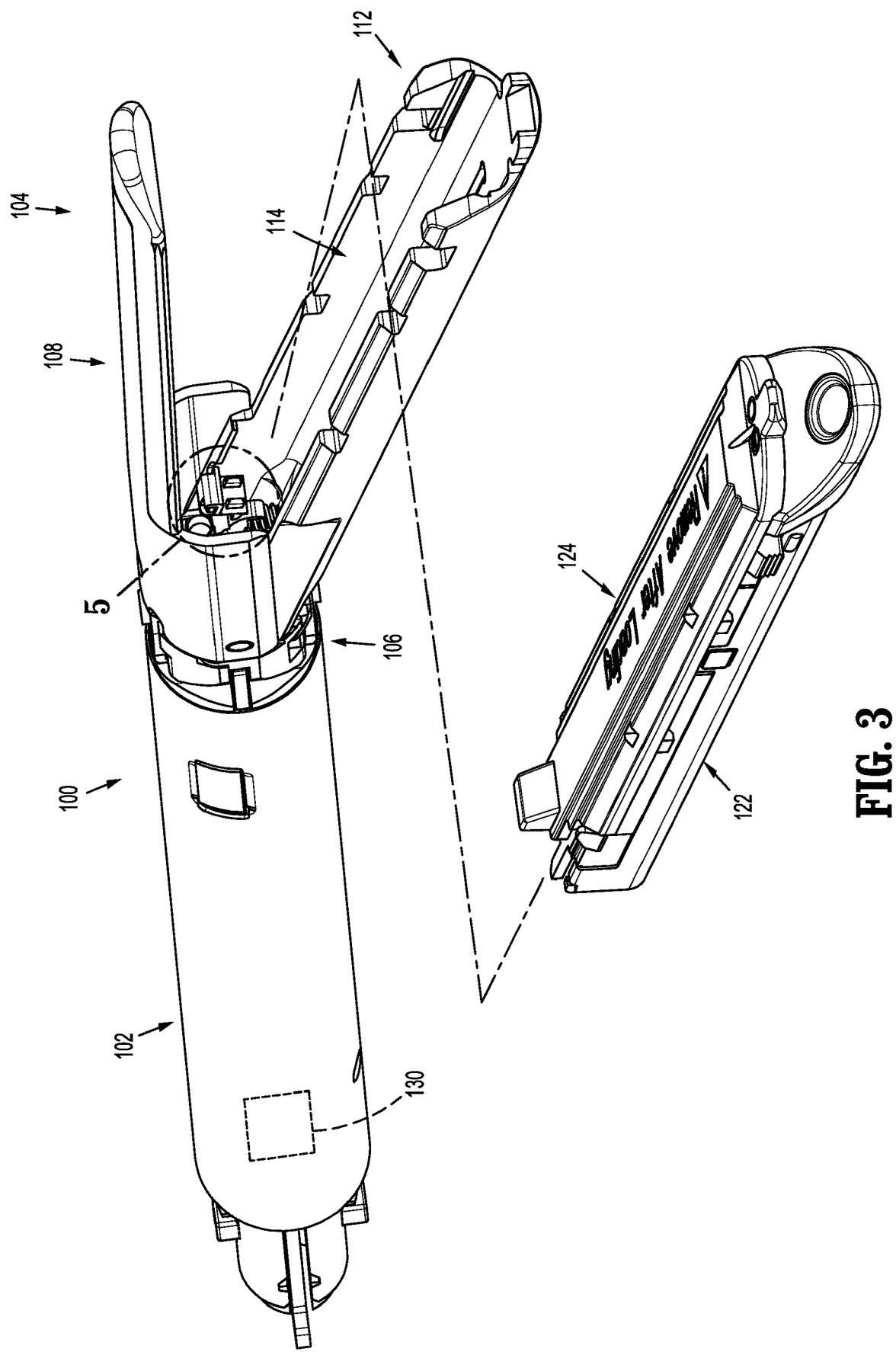
FIG. 3 is a side, perspective view of the surgical loading unit of FIG. 2, illustrating a staple cartridge assembly of the surgical loading unit in a disassembled state.

FIGS. 1-3 illustrate the surgical loading unit 100 which includes a proximal body portion 102 and an end effector assembly 104. A mounting assembly 106 is secured to the end effector assembly 104 and is pivotally coupled to the proximal body portion 102 of the loading unit 100 to pivotally secure the end effector assembly 104 to the proximal body portion 102. Although the end effector assembly 104 is shown and described as being operable by the surgical handle assembly 12 (FIG. 1), it is envisioned that the end effector assembly 104 may also be operably coupled to a surgical robotic instrument.

The end effector assembly 104 includes a first jaw member, such as, for example, an anvil assembly 108, and a second jaw member, such as, for example, a staple cartridge assembly 110, which are movable in relation to each other between approximated and expanded or open configurations. The cartridge assembly 110 generally includes a chassis 112 (FIG. 3) and a disposable staple cartridge body 122 configured for removable receipt in the chassis 112. The chassis 112 has a proximal end portion pivotably coupled to a proximal end portion of the anvil assembly 108. In embodiments, the proximal end portion of the chassis 112 may be indirectly pivotably coupled to the anvil assembly 108. The chassis 112 defines an elongate channel 114 (FIG. 3) therein dimensioned for removable receipt of the staple cartridge body 122.

The staple cartridge body 122 has a tissue-contacting surface 116 (FIG. 2) defining a plurality of rows of staple-retaining slots. The staple cartridge body 122 supports a plurality of staples (not shown) therein. The loading unit includes a firing member that is configured to interact with a sled having sloped wedges, and pushers with corresponding cam surfaces, tp discharge the staples through respective staple-retaining slots formed in the tissue-contacting surface 116. The firing member moves through the staple cartridge body 122 to discharge the rows of staples in a sequential manner. The staple cartridge assembly 110 may further include a shipping wedge 124 (FIG. 3) configured to maintain the staples within the staple-retaining slots of the tissue-contacting surface 116 of the staple cartridge body 122 and prevent actuation of the end effector assembly 104 prior to removal of the shipping wedge 124.

The surgical loading unit 100 includes a memory 130 (FIG. 2) disposed within the proximal body portion 102. In aspects, the memory 130 may be disposed at any other suitable location of the surgical loading unit 100, such as within or on the anvil assembly 108 or the staple cartridge assembly 110. The memory 130 is configured to communicate to the handle assembly 12 a presence of the surgical loading unit 100 and one or more operating parameters of the surgical loading unit 100 via electrical contacts or a wireless connection (e.g., near field communication), upon engagement of the surgical loading unit 100 with the adapter assembly 14.

The memory 130 may include an EEPROM, EPROM, or any suitable non-transitory storage chip that stores programs or sets of instructions for the operation of the surgical loading unit 100. Such programs may store operating parameters of the surgical loading unit 100, such as, for example, firing parameters that need to be achieved to successfully apply a staple or clip to tissue. The firing parameters stored in the memory 130 may include a staple firing speed of the surgical loading unit 100, a staple firing force of the surgical loading unit 100, a clamping speed of the end effector assembly 104 of the surgical loading unit 100, and/or a clamping force of the end effector assembly 104 of the surgical loading unit 100. Other operating parameters may be stored in the memory 130 of the surgical loading unit 100, such as, for example, tissue thickness indications or knife retraction speeds. Software updates or revisions may also be stored in the memory 130 to allow for modification or a complete redesign of the software stored in the memory 4 (FIG. 1) of the handle assembly 12.

The disclosure provides a plurality of surgical loading units 100 with each configured to be used on a specific type of tissue (e.g., liver, lung, heart, gastrointestinal, etc.) and/or during a specific type of surgical procedure (e.g., liver resection, gastro-intestinal anastomosis, lesion resection). As such, each of the loading units 100 has a discrete set of operating parameters that are unique to the type of tissue on which the selected surgical loading unit 100 is to be used on and/or the type of surgical procedure that the surgical loading unit 100 is to perform. The operating parameters may override operating parameters stored in programming in the handle assembly 12, such that upon coupling a selected loading unit 100 to the handle assembly 12, the pre-set programming in the handle assembly 12 for operating surgical loading units is overridden and directed to carry out the operating parameters stored in the memory 130 of the selected surgical loading unit 100. It is contemplated that while each of the loading units 100 has stored therein unique operating parameters, the surgical loading units 100 may have identical structural components.

The memory 130 of the surgical loading unit 100 may also be configured to provide data about the surgical loading unit 100 to the processor 2 of the handle assembly 12 in response to electromechanically coupling the surgical loading unit 100 to the handle assembly 12. The data may include at least one of a serial number of the surgical loading unit 100, a type of the surgical loading unit 100, a size of the surgical loading unit 100, a staple size used in the surgical loading unit 100, information identifying whether the surgical loading unit 100 has been fired, a maximum number of uses of the surgical loading unit 100, a length of a firing stroke of the surgical loading unit 100, and combinations thereof. Knowing a length of the firing stroke of the surgical loading unit 100 allows the processor 2 to determine when to stop firing the surgical loading unit 100. The firing stroke can include the length of the staple line, the cut line of the knife (if the instrument has one), or simply the desired end of travel for the firing member.

In operation, a particular surgical loading unit 100 is selected depending on the type of surgical procedure to be performed and/or the type of tissue being operated on. For example, if the surgical procedure involves a liver resection, the surgical loading unit 100 having operating parameters catered to resecting liver tissue is selected. Due to liver tissue being highly vascular and thick, the surgical loading unit 100 for liver resection may be pre-programmed with instructions, which when executed, result in a fast and constant staple firing speed regardless of a sensed tissue thickness. If another type of tissue or surgical procedure is to be performed, a loading unit equipped with the appropriate operating parameters would be selected instead of the surgical loading unit 100 used for liver resection.

Figure 4:
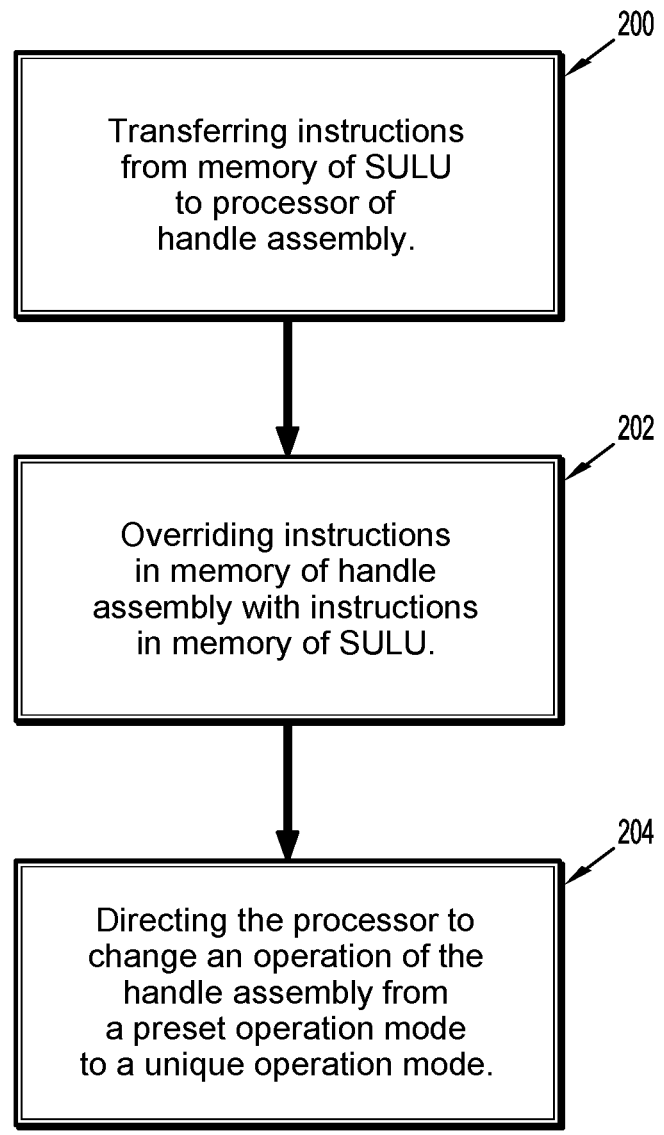
FIG. 4 is a flow diagram illustrating an exemplary method of operating the surgical stapling instrument of FIG. 1.

Upon coupling the selected surgical loading unit 100 to the adapter assembly 14 (FIG. 1), an operation of the surgical stapling instrument 10 is modified. In particular, with reference to FIG. 4, in step 200, the instructions or programs are transferred from the memory 130 (FIG. 2) of the surgical loading unit 100 to the processor 2 (FIG. 1) of the powered handle assembly 12. In step 202, the programming stored in the memory 4 of the handle assembly 12 are overridden with the instructions of the memory 130 of the surgical loading unit 100. Absent an override from the instructions of the surgical loading unit 100, the programming of the handle assembly 12, when executed by the processor 2, would cause the surgical stapling instrument 10 to automatically and dynamically adjust a firing speed based on a sensed tissue thickness.

In step 204, the instructions of the memory of the surgical loading unit direct the processor 2 to change an operation of the adapter assembly 14 or the handle assembly 12 from a preset operation mode to a unique operation mode. The unique operation mode adjusts how the handle assembly 12 or the adapter assembly 14 affects functions of the surgical loading unit 100. For example, with the surgical loading unit 100 for liver resection attached to the adapter assembly 14, the instructions from the surgical loading unit 100 direct the processor 2 to fire staples at a constant and fast speed into the liver tissue rather than adjusting the firing speed based on tissue thickness to minimize bleeding during the surgical procedure.

Although described with respect to the adapter assembly 14 and the surgical loading unit 100, different adapter assemblies configured for use with different surgical loading units and/or different surgical loading units configured for use with the adapter assembly 14 are also capable of being used with the handle assembly 12. Suitable surgical loading units configured for use with the adapter assembly 14 and/or other adapter assemblies usable with the powered handle assembly 12 include surgical loading units configured for performing endoscopic gastro-intestinal anastomosis (EGIA) procedures, e.g., the surgical loading unit 100 or a multi-use loading unit ("MULU") (not shown), surgical loading units configured to perform end-to-end anastomosis (EEA) procedures, transverse stapling loading units, and curved loading units.

Persons skilled in the art will understand that the instruments and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

The invention claimed is:

1. A surgical loading unit for use with a surgical stapling instrument, the surgical loading unit comprising:
   a staple cartridge assembly;
   an anvil assembly operably coupled to the staple cartridge assembly; and
   a memory associated with at least one of the staple cartridge assembly or the anvil assembly, the memory having stored therein instructions, which when executed, direct a processor to adapt an operation of an adapter assembly or a handle assembly from a preset operation mode to a unique operation mode, wherein the preset operation mode includes automatically adjusting a staple firing speed of the surgical loading unit based on a sensed tissue thickness, and the unique operation mode includes setting a constant staple firing speed of the surgical loading unit.

2. The surgical loading unit according to claim 1, wherein the memory further has stored therein data related to the surgical loading unit.

3. The surgical loading unit according to claim 2, wherein the data includes at least one of a serial number of the surgical loading unit, a type of the surgical loading unit, a size of the surgical loading unit, a staple size included in the surgical loading unit, information identifying whether the surgical loading unit has been fired, a length of a firing stroke of the surgical loading unit, or a maximum number of uses of the surgical loading unit.

4. A surgical stapling instrument, comprising:
a handle assembly including:
   a memory having stored therein instructions; and
   a processor configured to execute the instructions; and
a surgical loading unit configured to be coupled to the handle assembly, the surgical loading unit including:
a staple cartridge assembly;
an anvil assembly operably coupled to the staple cartridge assembly; and
a memory having stored therein instructions, which when executed by the processor of the handle assembly, override the instructions stored in the memory of the handle assembly and direct the processor to adapt an operation of an adapter assembly or the handle assembly from a preset operation mode to a unique operation mode, wherein the preset operation mode includes automatically adjusting a staple firing speed of the surgical loading unit based on a sensed tissue thickness, and the unique operation mode includes setting a constant staple firing speed of the surgical loading unit.

5. The surgical stapling instrument according to claim 4, wherein the memory of the surgical loading unit further has stored therein data related to the surgical loading unit.

6. The surgical stapling instrument according to claim 5, wherein the data includes at least one of a serial number of the surgical loading unit, a type of the surgical loading unit, a size of the surgical loading unit, a staple size, information identifying whether the surgical loading unit has been fired, a length of a firing stroke of the surgical loading unit, or a maximum number of uses of the surgical loading unit.

7. The surgical stapling instrument according to claim 4, further comprising the adapter assembly, the adapter assembly being configured to interconnect the surgical loading unit and the handle assembly.

8. A method of modifying an operation of a surgical stapling instrument, the method comprising:
transferring instructions from a memory of a surgical loading unit to a processor of an adapter assembly or a powered handle assembly of the surgical stapling instrument;
overriding instructions stored in a memory of the handle assembly or the adapter assembly with the instructions of the memory of the surgical loading unit, wherein the instructions of the memory of the surgical loading unit direct the processor to adapt an operation of the adapter assembly or the handle assembly from a preset operation mode to a unique operation mode, wherein the preset operation mode includes automatically adjusting a staple firing speed of the surgical loading unit based on a sensed tissue thickness, and the unique operation mode includes setting a constant staple firing speed of the surgical loading unit.

* * * * *